(12) United States Patent
Bechtold et al.

(10) Patent No.: US 6,837,859 B2
(45) Date of Patent: *Jan. 4, 2005

(54) SHOCK WAVE SOURCE WITH A COIL CARRIER HAVING A NON-CIRCULAR CONTOUR

(75) Inventors: Mario Bechtold, Röttenbach (DE); Jens Fehre, Hausen (DE); Bernd Granz, Oberasbach (DE); Matthias Mahler, Erlangen (DE)

(73) Assignee: Siemens Aktiengesellschaft, Münich (DE)

( * ) Notice: Subject to any disclaimer, the term of this patent is extended or adjusted under 35 U.S.C. 154(b) by 34 days.

This patent is subject to a terminal disclaimer.

(21) Appl. No.: 10/238,567

(22) Filed: Sep. 10, 2002

(65) Prior Publication Data

US 2003/0065279 A1 Apr. 3, 2003

(30) Foreign Application Priority Data

Sep. 10, 2001 (DE) ......................... 101 44 422

(51) Int. Cl.[7] .............................................. A61B 17/00
(52) U.S. Cl. ..................... 601/4; 310/327; 367/162; 367/176; 181/207; 181/208; 181/209
(58) Field of Search .................. 601/2, 4; 181/207, 181/208, 209, 210; 600/439; 310/327; 604/22; 367/240, 162, 176; 381/71.2

(56) References Cited

U.S. PATENT DOCUMENTS

| 4,721,106 A | * | 1/1988 | Kurtze et al. ................... 601/4 |
| 4,807,627 A | * | 2/1989 | Eisenmenger .................. 601/4 |
| 4,972,826 A | * | 11/1990 | Koehler et al. ................ 601/4 |
| 5,394,786 A | * | 3/1995 | Gettle et al. .................... 86/50 |
| 6,302,857 B1 | * | 10/2001 | Landeck ......................... 601/4 |
| 2003/0060738 A1 | * | 3/2003 | Ein-gal ........................... 601/4 |

FOREIGN PATENT DOCUMENTS

| DE | 35 05 855 | 8/1986 |
| DE | G 86 18 166.1 | 7/1988 |
| EP | 0 189 781 | 1/1986 |

* cited by examiner

Primary Examiner—Eleni Mantis Mercader
(74) Attorney, Agent, or Firm—Schiff Hardin LLP

(57) ABSTRACT

A shock wave source has a coil carrier, having a longitudinal axis, a coil and a metallic membrane separated from the coil in insulating fashion for generating shock waves. The coil carrier has a generated surface, a first cover surface facing toward the coil and a second cover surface facing away from the coil. For reducing the low-frequency sound generation when generating shock waves, a cross-sectional area of the coil carrier intersected at a right angle by the longitudinal axis has a non-circular contour. A reduction of the audible sound generation when generating shock waves can also be achieved when the second cover surface of the coil carrier is non-flat.

16 Claims, 3 Drawing Sheets

SHOCK WAVE SOURCE WITH A COIL CARRIER HAVING A NON-CIRCULAR CONTOUR

BACKGROUND OF THE INVENTION

1. Field of the Invention

The present invention is directed to a shock wave source of the type having a coil carrier, a coil and a metallic membrane separated from the coil in insulating fashion for generating shock waves.

2. Description of the Prior Art

Electromagnetic shock wave sources of the type described above are utilized, for example, in medicine for the non-invasive disintegration of body calculi of a patient, for example for the disintegration of kidney stones. The generation of shock waves with such a shock wave source is accomplished by a brief-duration high-voltage pulse applied to the coil arranged on the coil carrier. As a result of the electromagnetic interaction of the coil with the metallic membrane separated from it in insulating fashion, the membrane is repelled from the coil in an enclosed volume of water located between the shock wave source and the patient. As a result, attenuated sine waves are emitted into the water as carrier medium between the shock wave source and the patient. Shock waves ultimately arise due to non-linear effects in the carrier medium, water. The attenuated sine oscillations have a basic frequency of about 150 through 200 kHz that is determined by the electrical properties of the shock wave source. The sine waves lie outside the human hearing range.

Nevertheless, audible waves arise when generating shock waves with an electromagnetic shock wave source—as described, moreover, in structure and function in, for example, H. Reichenberger, G. Naser, "Electromagnetic Acoustic Source for the Extracorporeal Generation of Shock Waves in Lithotripsy", Siemens Forschungs-und Entwicklungsberichte, 15, 1986, No. 4, pages 187 through 194. Simultaneously with the emission of the sine waves into the water path, waves propagate in the opposite direction in the coil carrier (usually formed of ceramic) that can convert initially axially propagating waves into radial or plate waves. The radial or plate waves cause the coil carrier to oscillate such that low-frequency waves arise in the human hearing range, i.e. below 20 kHz. Due to the highly symmetrical geometrical shape of the coil carrier (the coil carrier usually has a circular cross-section in planes at a right angle to its longitudinal axis) equiphase superimpositions of radial and plate waves also occur due to reflections at the edge of the coil carrier. As a result, audible waves arise that have a very unpleasant sound level for patients and medical personnel.

SUMMARY OF THE INVENTION

An object of the present invention to provide a shock wave source of the type initially described wherein the generation of audible acoustic waves is reduced in the generation of shock waves.

This object is inventively achieved in a shock wave source having a coil carrier with a longitudinal axis, a metallic coil and having a membrane separated from the coil in insulating fashion for generating shock waves, wherein the coil carrier is fashioned such that a cross-sectional area of the coil carrier intersected at a right angle by its longitudinal axis has a non-circular contour. Inventively, this design of the coil carrier represents a rejection of a high degree of symmetry of the coil carrier. This high degree of symmetry contributes to the disadvantage of radial or plate waves forming during the course of generating shock waves superimposing equiphase due to reflections at the edges of the coil carrier, causing the coil carrier to be excited to pronounced oscillations, and thus causing acoustic waves having a higher sound level to be generated. By departing from this high degree of symmetry, the equiphase superimposition of, in particular, radial waves and plate waves is at least reduced, so that the generation of acoustic waves with high sound level is also reduced.

In versions of the invention the cross-sectional area of the coil carrier can have a contour with corners, an irregularly proceeding contour, or a regularly proceeding, noncircular contour that can have corners and rounded portions. As a result, equiphase superimpositions of radial waves and plate waves are prevented or at least significantly reduced, as already mentioned.

The object also is inventively achieved in a shock wave source having a coil carrier, a coil, and a metallic membrane separated from the coil in insulating fashion for generating shock waves, the coil carrier having a generated surface, a first cover surface thereof facing toward the coil and a second cover surface thereof facing away from the coil, with the second cover surface fashioned non-flat. As a result of this design of the second cover surface, the conversion of axially propagating waves into radial or plate waves can be noticeably reduced. Moreover, equiphase superimposition of radial or plate waves can be reduced, so that there is a reduction on the excitation of the coil carrier to oscillate and, accordingly, the generation of acoustic waves is noticeably reduced.

In versions of the invention, the second cover surface has depressions and/or elevations that can contain round or polygonal shapes and are preferably irregular.

According to one embodiment of the invention, the coil carrier is additionally formed of a material that damps the formation and/or propagation of waves. Differing from a coil carrier formed of a ceramic material as disclosed, for example, in German OS 35 02 770 and German OS 35 05 855, a coil carrier fashioned of a material that damps the formation and/or the propagation of waves additionally reduces the generation of acoustic waves in the generation of shock waves, since it is not only the axial propagation of high-frequency waves having a basic frequency between approximately 100 and 200 kHz in the direction of the coil carrier that is damped, but also their conversion into low-frequency radial waves or plate waves. Thus the formation of radial waves or plate waves that cause the coil carrier to oscillate, as well as their propagation, are both noticeably reduced. Accordingly, the coil carrier is excited less to oscillate, and thus noticeably fewer acoustic waves are generated in the generation of shock waves.

In one version of the invention the material of the coil carrier that damps the formation and/or propagation of waves has a mechanical vibrational Q of less than 100, preferably less than 50. The value of Q is a criterion for the capability of a material to oscillate. In comparison thereto, the ceramic material conventionally employed for coil carriers has a Q of approximately 1000.

In further embodiments of the invention the material for the coil carrier contains rubber or plastic. The coil carrier can alternatively be entirely fashioned of rubber or plastic. The material preferably is provided with electrically non-conductive particles in order to obtain a heterogeneous material that usually damps the formation and/or the propagation of waves better than a homogeneous material. According to a further version of the invention, the particles are formed of a material that has a higher hardness than the material that damps the formation and/or the propagation of waves. A higher strength, and thus a higher dimensional stability of the coil carrier, are achieved in this way.

In another embodiment of the invention the material damping the formation and/or the propagation of waves is an expanded plastic. A suitable expanded plastic is, for example, PUR high-resistance foam as distributed by IVPU Industrieverband, Polyurethan-Hartschaum e.V., Stuttgart.

In a further version of the invention, the material that damps the formation and/or the propagation of waves has a honeycomb structure. The material is plastic or resin-bonded paper according to one version of the invention. The honeycomb structure can be composed of regular and/or irregular polygons. A suitable material of plastic or resin-bonded paper having a honeycomb structure is distributed, for example, by Euro-Composites, Zone Industrielle, Luxemburg. A coil carrier that is fashioned of such a material having a honeycomb structure also noticeably reduces the formation of low-frequency waves and noticeably damps the propagation of low-frequency and high-frequency waves. As a result the generation of acoustic waves is significantly reduced when generating shock waves.

DESCRIPTION OF THE PREFERRED EMBODIMENTS

Figure 1:
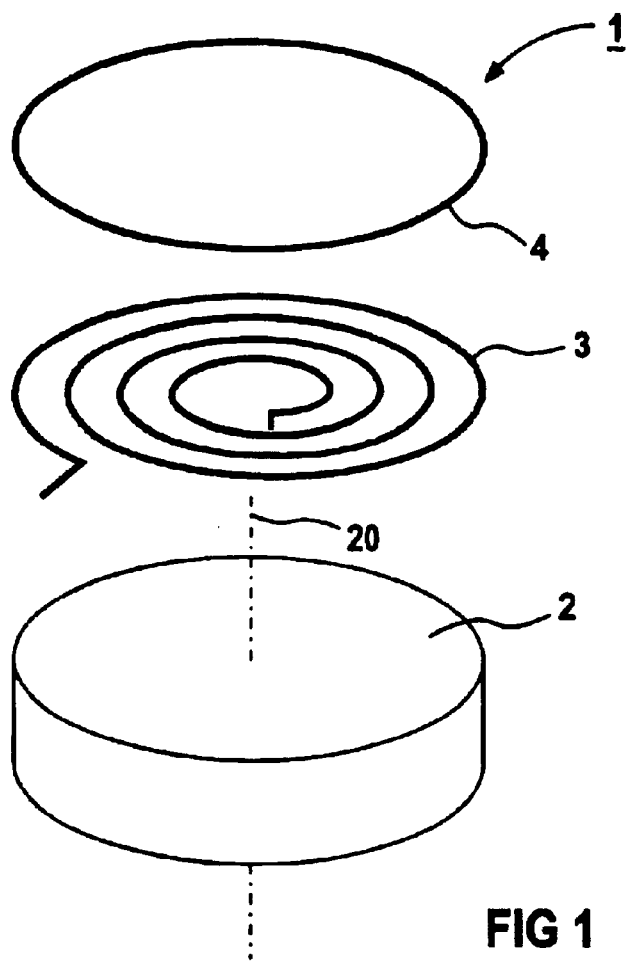
FIGS. 1 and 2 are schematic illustrations showing the structure of an electromagnetic shock wave source having a coil carrier.
Figure 2:
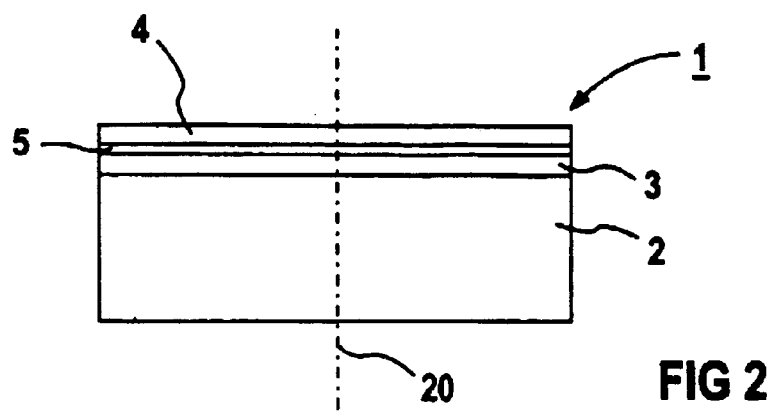

FIG. 1 shows a highly schematic illustration of the components of a known electromagnetic shock wave source 1. In the exemplary embodiment, the shock wave source 1 has a disk-shaped coil carrier 2, a flat coil 3 and a metallic membrane 4. For illustrating the structure of the shock wave source 1, the coil carrier 2, the flat coil 3 and the membrane 4 are shown separated in FIG. 1. In the operational state of the shock wave source 1 shown in FIG. 2, the flat coil 3 lies on the coil carrier 2 and is separated from the metallic membrane 4 in insulating fashion by an insulating foil 5 (not shown in FIG. 1). When generating shock waves, a brief-duration high-voltage pulse is applied to the flat coil 3 arranged on the coil carrier 2. Due to the electromagnetic interaction of the flat coil 3 with the membrane 4 separated therefrom in insulating fashion, this is repelled into an acoustic propagation medium (not explicitly shown in FIGS. 1 and 2), which is usually water. A shock wave is generated in this way; and can be introduced into the body of a patient via the propagation medium, water.

Since, as already initially mentioned, acoustic waves with an unpleasant sound level are also generated when generating shock waves with such an electromagnetic shock wave source, in accordance with the invention the geometry of the coil carrier is modified, so that no or only insignificant equiphase superimpositions of radial or plate waves occur that cause the coil carrier to oscillate.

Figure 3:
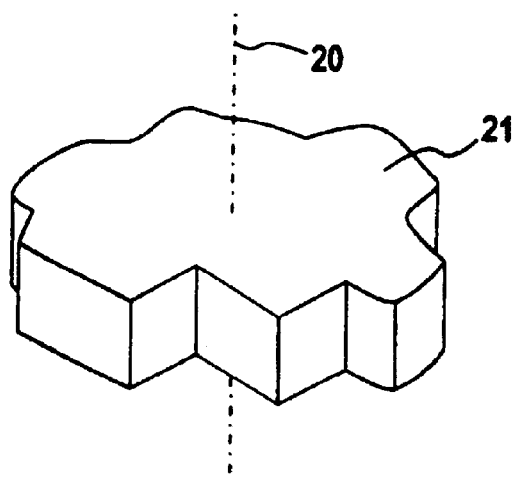
FIGS. 3 through 8 show inventive embodiments of a coil carrier for use in the shock wave source from FIGS. 1 and 2.
Figure 4:
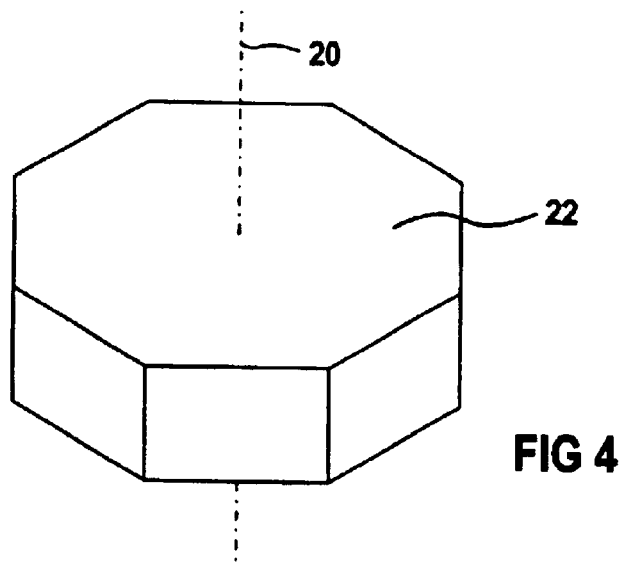

FIGS. 3 and 4 show inventive embodiments of coil carriers 21 and 22. The coil carriers 21 and 22 are characterized by a design that represents a departure from the conventional high degree of symmetry. As can be seen, the coil carrier 2 of FIG. 1 has a longitudinal axis 20. The conventional coil carrier 2 has a high symmetry with respect to the longitudinal axis 20. An arbitrary cross-sectional area of the coil carrier 2 intersected by the longitudinal axis at a right angle has a round contour, i.e. a contour with a high degree of symmetry. No modification of its outside contour, given a plan view onto the coil carrier 2, occurs when the cross-sectional area or the coil carrier 2 is rotated around the longitudinal axis 20. This disadvantageously favors the equiphase superimposition of radial or plate waves forming during the generation of shock waves. and thus promotes a generation of low-frequency acoustic waves with high sound level.

In accordance with the invention a cross-sectional area of the coil carrier intersected by the longitudinal axis 20 at a right angle has a non-circular contour, so that the final contour generally does not coincide with the initial contour as a result of an arbitrary rotation of the cross-sectional area or the coil carrier around the longitudinal axis 20. Such contour is recognizable given a plan view onto the cross-sectional area or the coil carrier.

The coil carrier 21 shown in FIG. 3 is fashioned such that an arbitrary cross-sectional area that is intersected by the longitudinal axis 20 at a right angle has a non-circular contour, a contour with corners in the present case. Thus, when radial or plate waves form, these are not reflected at the edges of the coil carrier 21 and equiphase superimpositions of these waves is precluded. If such equiphase superimpositions were permitted to occur, an amplification of the waves. and thus an intensified sound generation, would arise. The coil carrier 21 is fashioned such that the final contour corresponds to the initial contour only given a rotation by 360° around the longitudinal axis 20.

FIG. 4 shows a coil carrier 22 having a cross-sectional area intersected by the longitudinal axis 20 at a right angle exhibiting a regularly fashioned, octagonal contour. Even though the contour is regular, the superimposition of plate or radial waves can be reduced by means of a departure from the round contour. However, the irregularly proceeding contour as shown in FIG. 3 is even more effective in view of avoiding such superimpositions than the fashioning of a coil carrier shown in FIG. 4.

The contour of a cross-sectional area intersected by the longitudinal axis 20 at a right angle need not, moreover, have only corners but can also have rounded portions.

Figure 5:
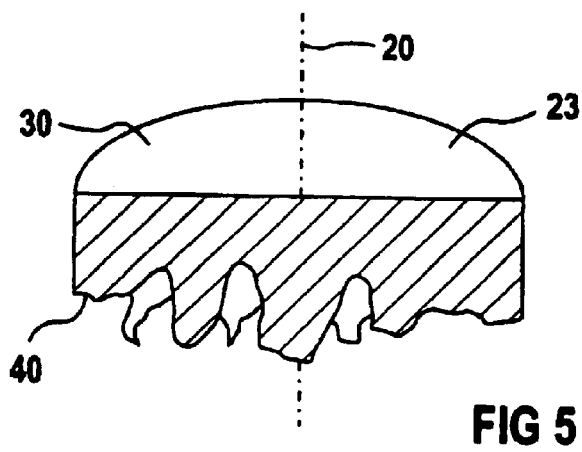

In another inventive embodiment of the coil carrier, the cover surface of the disk-shaped coil carrier facing away from the flat coil 3 is fashioned non-flat. FIG. 5 shows a section through an inventive coil carrier 23 in the direction of the longitudinal axis 20. As can be seen from FIG. 5, that cover surface 30 that faces toward the flat coil 3 and on which the flat coil 3 is arranged, is flat. In contrast thereto, the second cover surface 40 of the coil carrier 23 facing away from the flat coil 3 is non-flat, provided with noticeable depressions and elevations in the present case. The depressions and/or elevations preferably are irregular. The depressions and/or elevations preferably extend over the entire cover surface. Thus, when generating shock waves, the waves propagating axially in the direction of the longitudinal axis 20 in the coil carrier 23 are converted into plate or radial waves to a reduced extent, if not at all. Also achieved is that no or only a few equiphase superimpositions of axially propagating waves occur that could cause the coil carrier to oscillate. The generation of low-frequency acoustic waves in the generation of shock waves is thus significantly reduced in this way.

In order to additionally reduce the generation of audible acoustic waves when generating shock waves, the coil carrier can be formed of a material that damps the formation of low-frequency waves and/or the propagation of high-frequency and low-frequency waves, so that the coil carrier is not excited to oscillate, or is at least excited to oscillate only in a greatly diminished way, and thus no or at least noticeably fewer acoustic waves arise when generating shock waves. The material should have a Q of below 100, preferably below 50.

Figure 6:
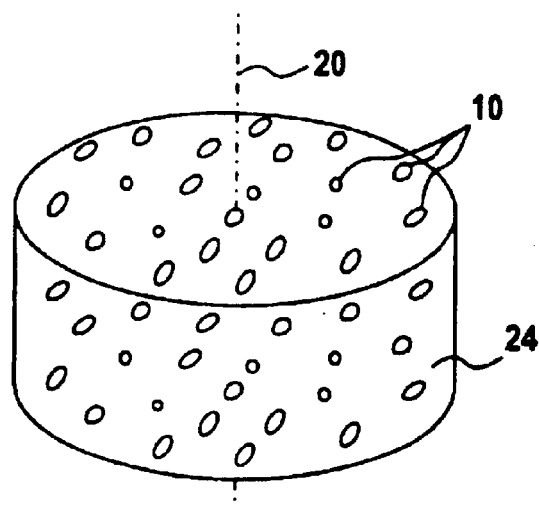
Figure 7:
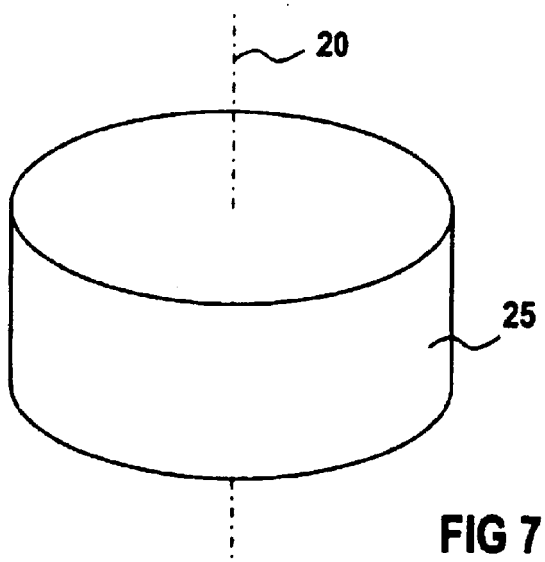
Figure 8:
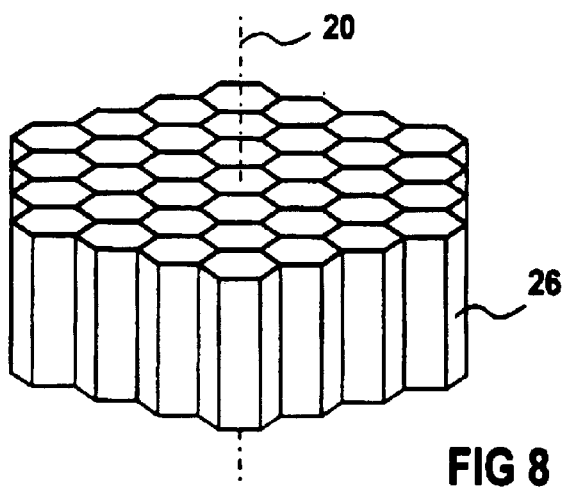

FIGS. 6 through 8 show coil carriers 24 through 26 that are fashioned of such materials that damp the formation and/or propagation of waves and have a vibrational Q of below 50. The coil carrier 24 shown in FIG. 6 is formed of rubber or plastic and is laced with hard, electrically non-conductive particles 10. In the exemplary embodiment, the particles are of tungsten oxide or ceramic, which exhibit a higher hardness than rubber or plastic. The particles are provided in order to increase the strength of the coil carrier 24 and keep it dimensionally stable as well as to form a heterogeneous material that usually damps the formation and propagation of waves even better than rubber or plastic alone.

FIG. 7 shows a coil carrier 25 that is fashioned of an expanded plastic. In the exemplary embodiment, the expanded plastic is a PUR high-resistance foam that is commonly utilized as a heat-damping material. PUR high-resistance foam, however, is also suitable as material for a coil carrier since the formation and propagation of waves is damped in the coil carrier 25 when generating shock waves, so that noticeably fewer acoustic waves are generated when generating shock waves compared to a coil carrier that is formed of ceramic.

FIG. 8 shows a third inventive embodiment of a coil carrier composed of a material comprising a honeycomb structure. The material forming the honeycomb structure can be plastic, resin-bonded paper or some other material. For example, Euro-Composites, Luxemburg, distributes such a material having a honeycomb structure. The formation and propagation of waves also can be damped with a coil carrier 26 fashioned of such a material, so that audible acoustic waves are generated only to a greatly reduced extent when generating shock waves with a shock wave source employing the coil carrier 26. The honeycomb structure can be formed by regular polygons, i.e. triangles, quadrangles or—as in the case of the exemplary embodiment—hexagons and/or irregular polygons, which are understood to be polygons having an irregular edge course.

Inventive developments of a coil carrier for an electromagnetic shock wave source have been presented and explained independently of one another above on the basis of FIGS. 3 through 8. The various embodiments of the coil carrier, however, can be combined with one another in arbitrary ways. For example, the coil carrier can be composed of PUR high-resistance foam, can have a polygonal, irregular outside contour in plan view, and the second cover surface thereof facing away from the flat coil can be provided with depressions and elevations. Other combinations of the embodiments of an inventive coil carrier explained individually in FIGS. 3 through 8 also can be unproblematically formed.

The coil carrier, moreover, need not necessarily be disk-shaped, nor need the coil be a flat coil.

Although modifications and changes may be suggested by those skilled in the art, it is the intention of the inventors to embody within the patent warranted hereon all changes and modifications as reasonably and properly come within the scope of their contribution to the art.

We claim as our invention:

1. A shock wave source comprising:

a coil carrier;

a coil disposed on said coil carrier;

a membrane overlying said coil on said coil carrier and separated from said coil in electrically insulating fashion, said coil being disposed between said carrier and said membrane and interacting with said membrane, upon being charged with current, for generating shock waves; and said coil carrier having a longitudinal axis and a cross-sectional area intersected by said longitudinal axis at a right angle having a non-circular contour.

2. A shock wave source as claimed in claim 1 wherein said contour of said cross-sectional area of said coil carrier has corners.

3. A shock wave source as claimed in claim 1 wherein said contour of said cross-sectional area of said coil carrier is an irregular contour.

4. A shock wave source as claimed in claim 1 wherein said contour of said cross-sectional area of said coil carrier is a regular, and non-circular contour.

5. A shock wave source as claimed in claim 1 said coil carrier has a first cover surface facing toward said coil and a second cover surface facing away from said coil, said second cover surface being non-flat.

6. A shock wave source as claimed in claim 5 wherein said second cover surface comprises structures selected from the group consisting of depressions and elevations.

7. A shock wave source as claimed in claim 6 wherein said structures are irregular.

8. A shock wave source as claimed in claim 5 wherein said coil carrier is comprised of a material which damps at least one of formation and propagation of waves in said coil carrier generated together with said shock waves.

9. A shock wave source as claimed in claim 8 wherein said material has a mechanical vibrational Q of below 100.

10. A shock wave source as claimed in claim 8 wherein said material is selected from the group consisting of rubber and plastic.

11. A shock wave source as claimed in claim 8 wherein said material contains particles.

12. A shock wave source as claimed in claim 11 wherein said particles have a hardness that is higher than said material.

13. A shock wave source as claimed in claim 8 wherein said material is expanded plastic.

14. A shock wave source as claimed in claim 8 wherein said material has a honeycomb structure.

15. A shock wave source as claimed in claim 14 wherein said honeycomb structure is comprised of polygons selected from the group consisting of regular polygons and irregular polygons.

16. A shock wave source as claimed in claim 14 wherein said material having said honeycomb structure is selected from the group consisting of plastic and resin-bonded paper.

* * * * *